United States Patent [19]

Chang et al.

[11] Patent Number: 5,035,898

[45] Date of Patent: * Jul. 30, 1991

[54] POTASSIUM/MAGNESIUM SUPPLEMENT

[75] Inventors: Richard R. Chang, Miramar; Edward M. Rudnic, Boca Raton, both of Fla.

[73] Assignee: Schering Corporation, Kenilworth, N.J.

[*] Notice: The portion of the term of this patent subsequent to Sep. 5, 2006 has been disclaimed.

[21] Appl. No.: 125,831

[22] Filed: Nov. 27, 1987

[51] Int. Cl.$^5$ ............................................. A61K 9/28
[52] U.S. Cl. .................................... 424/474; 424/679
[58] Field of Search ............... 424/474, 153, 154, 156

[56] References Cited

U.S. PATENT DOCUMENTS

| | | | |
|---|---|---|---|
| 4,104,370 | 8/1978 | Bloch | 424/153 |
| 4,788,180 | 11/1988 | Bloch | 424/400 X |
| 4,863,743 | 9/1989 | Hsaio et al. | 424/400 |

FOREIGN PATENT DOCUMENTS

| | | |
|---|---|---|
| 72352 | 4/1970 | Fed. Rep. of Germany . |
| 2132923 | 1/1973 | Fed. Rep. of Germany . |
| 34127 | 2/1985 | Hungary . |
| 8603121 | 6/1986 | PCT Int'l Appl. . |
| 657967 | 10/1986 | Switzerland . |
| 1356096 | 6/1974 | United Kingdom . |
| 1356097 | 6/1974 | United Kingdom . |
| 1422193 | 1/1976 | United Kingdom . |

*Primary Examiner*—Thurman K. Page
*Assistant Examiner*—Robert H. Harrison
*Attorney, Agent, or Firm*—Anita Magatti; James Nelson

[57] ABSTRACT

Pharmacuetical compositions for administering a combination of controlled release potassium chloride and immediately-released magnesium salt are disclosed.

17 Claims, No Drawings

POTASSIUM/MAGNESIUM SUPPLEMENT

The present invention relates to a combination of potassium and magnesium-salts useful in the treatment of hypokalemia and hypomagnesemia. In particular, it relates to a combination of controlled release potassium chloride and an immediately-released magnesium salt, preferably magnesium oxide.

BACKGROUND

It is well known that mineral deficiencies such as hypokalemia and hypomagnesemia can occur for a variety of dietary or physiological reasons and often result from long term therapy with drugs such as thiazides and loop diuretics. Hypokalemia and hypomagnesemia can cause variety of unpleasant or dangerous symptoms including cardiac arrhythymias, weakness, fatigue and muscle cramps.

While the need for potassium and magnesium supplementation is well recognized, no combination supplements known to date have been completely successful. Potassium is known to cause irritation and/or ulceration in the gastric tract when taken orally, so combinations of salts such as the granulation described in UK Patent 1,356,096, which provides both potassium and magnesium in immediate release form, are likely to promote gastric upset.

Other known formulations wherein the release of both the potassium and magnesium are controlled, e.g. those described in U.S. Pat. No. 4,104,370 and UK patent 1,356,097, tend to promote the same gastric problems, but for the opposite reason. That is, wax-matrix formulations such as disclosed in the cited patents may not disintegrate rapidly or completely, causing high local concentrations of potassium injurious to the gastric tract. These wax-matrix tablets, as well as other controlled release formulations such as that described in German patent 2,132,923, wherein enteric coated capsules are disclosed, (which capsules in effect become immediate release formulations when the coating and capsule dissolve, thereby presenting the problems associated with non-controlled release potassium salts) further present the possibility of reduced bioavailability of magnesium. Magnesium is absorbed from the gastrointestinal tract in the region of the upper small bowel by means of an active process closely related to the transport system for calcium. Therefore, the use of magnesium in a controlled-release or enteric-release form would be inappropriate due to the reduced biavailability. Moreover, unlike potassium, the controlled release of magnesium is unnecessary since magnesium salts are not associated with gastrointestinal irritation and ulceration.

Furthermore, the above cited patents may not provide therapeutic doses of both potassium and magnesium. The dosages in the formulation in the cited patents range from a low of 0.25 to a high of 15 meq. for magnesium and from a low of 0.4 to a high of 10 meq. for potassium. However, the recommended daily dietary allowance for magnesium in adults is 25 to 33.4 meq (milliequivalent). The daily dose of magnesium required to prevent depletion in patients receiving diuretics has not yet been established, while a daily dose of 20 meq of potassium is typically used for the prevention of hypokalmia.

DETAILED DESCRIPTION

We have found that a combination of controlled release potassium chloride and an immediately-released magnesium salt provides the necessary physical and pharmacological characteristics to allow maximum efficacy.

In particular, the present invention relates to a combination of coated potassium chloride crystals and a magnesium salt, wherein the potassium chloride crystals are coated with a combination of ethylcellulose and at least one of hydroxypropylcellulose and polyethyleneglycol. The coated crystals are comprised of about 60 to 86.5% by weight of potassium chloride, about 9 to 15% by weight of ethylcellulose, and about 0.5 to 3% by weight of at least one of hydroxypropylcellulose and polyethylene glycol and preferably may comprise 0.5 to 2% of a lubricating agent such as magnesium stearate or stearic acid (all percentages based on the total weight of the coated crystals). The potassium chloride crystals have a mesh size of 30–50 mesh, preferably 40 mesh. Coated potassium chloride crystals as described above are disclosed in WO 86/04817, published Aug. 28, 1986, which claims priority of co-assigned U.S. Ser. No. 702,714, filed Feb. 19, 1985, now abandoned, and herein incorporated by reference. Such coated crystals, when introduced into the gastric tract, e.g., from a quickly-disintegrating tablet, are distributed by the peristaltic motion of the gut and do not allow undesirable locally high potassium chloride concentrations.

The magnesium salt is selected from pharmaceutically acceptable salts such as magnesium hydroxide, magnesium carbonate, magnesium sulfate, magnesium chloride, magnesium gluconate, magnesium phosphate, magnesium oxide, or a combination of such salts. High magnesium content salts are preferred, e.g., the hydroxide and oxide, since the final dosage form is therefore less bulky. Magnesium oxide is a preferred salt.

The coated potassium chloride crystal and magnesium salt mixture can be filled into capsules, either a conventional pharmaceutically acceptable capsule to be swallowed whole by the patient, or a capsule which may be opened by the patient. The latter capsules or packets (e.g., sealed cellophane envelopes) may be used to administer the mixture in liquid form (e.g., suspend the mixture in water or juice) or in soft food (e.g., sprinkle the mixture on applesauce).

The mixture of coated potassium chloride crystals and magnesium salt can also be compressed into tablets for oral administration. Such tablets may comprise conventional excipients, such as diluents, compression aids, disintegrants, lubricants, flavorings and coloring agents. Tablets of the present invention preferably comprise a compression aid such as micro-crystalline cellulose or lactose; a disintegrant such as crospovidone (cross-linked polyvinylpyrrolidone), a modified starch (e.g., sodium carboxymethyl starch), or a modified cellulose gum (e.g., croscarmellose sodium type A, N.F.); and a lubricating agent such as magnesium stearate or stearic acid. Preferred are microcrystalline cellulose as the compression aid, crospovidone as the disintegrant, and magnesium stearate as the lubricant. Concentration ranges (based on total tablet weight) of the excipients are about 4-20%, preferably about 6% compression aid; about 0.5 to 10%, preferably about 1% disintegrant; and 0 to about 1%, preferably about 0.5% lubricant.

Tablets may be prepared by conventional tabletting procedures.

Dosage forms of the present invention comprise a magnesium slat in an amount to provide about 7.5 to about 35 meq elemental magnesium per day, preferably about 7.5 to about 15 meq per day. The typical daily dose of potassium for the prevention of hypokalemia is 20 meq per day, and for the treatment of potassium deficiency, 40-100 meq per day. The lower concentration dosage forms of this invention may be taken in a single daily dose, but the higher dosages are preferably administered in divided dosages taken 2 to 4 times a day. Dosage forms of this invention thus comprise about 10 meq to about 20 meq potassium chloride and 7.5 to 35 meq of magnesium salt.

The following examples show the preparation of the coated potassium chloride crystals and several typical tablet formulations.

EXAMPLE 1

| POTASSIUM CHLORIDE COATED CRYSTALS | |
|---|---|
| Ingredients | Quantity/Batch |
| Potassium Chloride, USP | 850 g |
| Ethyl Cellulose, NF (Ethocel, Type 100) | 127.5 g |
| Hydroxypropyl Cellulose NF (Klucel L.F.) | 15 g |
| Magnesium Stearate NF | 7.5 g |
| *Methyl Alcohol NF | 560 g |
| *Methylene Chloride NF | 2820 g |
| TOTAL | 1000 g |

*Removed during process.

Method of Manufacture:

The potassium chloride crystals (30-50 mesh) are coated in a 6" Wurster fluidized bed column with 15% (w/w) of Ethocel® 100 and Klucel® L.F. are dissolved in a methylene chloride and methanol co-solvent system and magnesium stearate is then added to the polymer solution to form a suspension. The suspension is stirred throughout the coating process. The potassium chloride crystals are coated at a 60° inlet temperature. The spraying pressure is 1.5 bars and the spray speed is approximately 15 ml per minute.

| POTASSIUM CHLORIDE 10 meq/MAGNESIUM OXIDE 15 meq TABLETS | | | |
|---|---|---|---|
| Ingredients | Concentration Range (% wt.) | Preferred Concentration (% wt.) | Preferred mg/Tablet |
| Coated Potassium Chloride | 51.5-71.3 | 69.03 | 882.4 |
| Magnesium Oxide Granules | 17.5-24.2 | 23.47 | 300.0 |
| Microcrystalline Cellulose NF (Avicel pH 101) | 4.0-20.0 | 6.00 | 76.7 |
| Crospovidone NF (Polyplasdone XL) | 0.5-10.0 | 1.00 | 12.8 |
| Magnesium Stearate | 0-1.0 | 0.50 | 6.4 |
| | | | 1278.3 |

Method of Manufacture:

Mix the ingredients thoroughly in a suitable blender for 10-15 min. and compress into suitable-sized tablets using a suitable die and punch set with a compression force in the range of 4,000 to 10,000 psi.

EXAMPLE 3

| POTASSIUM CHLORIDE 10 meq/MAGNESIUM OXIDE 7.5 meq TABLETS | | | |
|---|---|---|---|
| Ingredients | Concentration Range (% wt.) | Preferred Concentration (% wt.) | Preferred mq/Tablet |
| Coated Potassium Chloride | 38.98-81.63 | 79.05 | 882.4 |
| Magnesium Oxide Granules | 10.03-13.88 | 13.44 | 150.0 |
| Microcrystalline Cellulose NF (Avicel pH 101) | 4.00-20.00 | 6.00 | 67.0 |
| Crospovidone NF (Polyplasdone XL) | 0.50-10.00 | 1.00 | 11.2 |
| Magnesium Stearate NF | 0-1.00 | 0.50 | 5.6 |
| | | | 1116.2 |

Prepare tablets as in Example 2.

EXAMPLE 4

| POTASSIUM CHLORIDE 18 meq/MAGNESIUM OXIDE 7.5 meq TABLETS | | | |
|---|---|---|---|
| Ingredients | Concentration Range (% wt.) | Preferred Concentration (% wt.) | Preferred mg/Tablet |
| Coated Potassium Chloride | 63.05-87.26 | 84.52 | 1588.2 |
| Magnesium Oxide Granules | 5.95-8.24 | 7.98 | 150.0 |
| Microcrystalline Cellulose NF (Avicel pH 101) | 4.00-20.00 | 6.00 | 112.7 |
| Crospovidone NF (Polyplasdone XL) | 0.50-10.00 | 1.00 | 18.8 |
| Magnesium Stearate NF | 0-1.00 | 0.50 | 9.4 |
| | | | 1879.1 |

Prepare tablets as in Example 2.

We claim:

1. A pharmaceutical composition for oral administration of potassium chloride and a magnesium salt comprising:
   7.5 to 35 milliequivalents of a pharmaceutically acceptable magnesium salt; and
   coated potassium chloride crystals comprising 10 to 20 milliequivalents of potassium chloride, wherein the coated potassium crystals are comprised of potassium chloride crystals being in the range of about 68% to about 86.5% by weight based on the total weight of the coated crystals and a coating material for the individual potassium chloride crystals, the coating material comprising in an amount in the range of about 9% to about 15% by weight based on the total weight of the coated crystals and at least one member selected from the groups consisting of hydroxypropylcellulose and polyethylene glycol in an amount in the range of about 0.5% to about 3% by weight based on the total weight of the coated crystals.

2. A composition of claim 1 wherein the coated potassium chloride crystals further comprise a lubricant in an amount in the range of about 0.5 to 2% by weight based on the coated crystal weight, wherein the lubricant is selected from the groups consisting of magnesium stearate and stearic acid.

3. A composition of claim 2 wherein the lubricant is magnesium stearate.

4. A pharmaceutical composition of claim 3 wherein the magnesium salt and the coated potassium chloride crystals are compressed to form a tablet.

5. A tablet of claim 4 further comprising a compression aid in an amount in the range of about 4–20%, preferably about 6% of total tablet weight, wherein the compression aid is selected from the groups consisting of microcrystalline cellulose and lactose.

6. A tablet of claim 5 wherein the compression aid is microcrystalline cellulose.

7. A tablet of claim 4 further comprising a disintegrant in an amount in the range of about 0.5 to 10%, preferably about 1% of the total tablet weight, wherein the disintegrant is selected from the groups consisting of crospovidone, modified starch, and modified cellulose gum.

8. A tablet of claim 7 wherein the disintegrant is crospovidone.

9. A tablet of claim 4 further comprising a lubricant in an amount in the range of 0 to about 1%, preferably about 0.5% of the total tablet weight, wherein the lubricant is selected from the groups consisting of magnesium stearate and stearic acid.

10. A tablet of claim 9 wherein the lubricant is magnesium stearate.

11. A tablet of claim 4 further comprising about 0.5 to 10% of a disintegrant, about 4–20% of a compression aid and 0 to about 1% of a lubricant, wherein said percentages are based on total tablet weight.

12. A composition of claim 1 wherein the magnesium salt and coated potassium chloride crystals are contained in a capsule.

13. A composition of claim 1 wherein the coated potassium chloride crystals are comprised of about 85% potassium chloride, about 12.5% ethylcellulose, about 1.5% hydroxypropylcellulose and about 0.75% magnesium stearate, wherein said percentages are based on the total weight of the coated crystals.

14. A composition of claim 13 in tablet form further comprising about 6% microcrystalline cellulose, about 1% crospovidone and about 0.5% magnesium stearate, wherein said percentages are based on total tablet weight.

15. A composition of claim 14 comprising 10 meq potassium chloride and 15 meq magnesium oxide.

16. A composition of claim 14 comprising 10 meq potassium chloride and 7.5 meq magnesium oxide.

17. A composition of claim 14 comprising 18 meq potassium chloride and 7.5 meq magnesium oxide.

* * * * *